United States Patent
Furuta et al.

(10) Patent No.: US 9,315,432 B2
(45) Date of Patent: Apr. 19, 2016

(54) PROCESS FOR PRODUCING 2, 3, 3, 3-TETRAFLUOROPROPENE AND 1, 1-DIFLUOROETHYLENE

(71) Applicant: ASAHI GLASS COMPANY, LIMITED, Chiyoda-ku (JP)

(72) Inventors: Shoji Furuta, Tokyo (JP); Yu Takeuchi, Tokyo (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 0 days.

(21) Appl. No.: 14/486,143

(22) Filed: Sep. 15, 2014

(65) Prior Publication Data

US 2015/0005538 A1    Jan. 1, 2015

Related U.S. Application Data

(63) Continuation of application No. PCT/JP2013/057258, filed on Mar. 14, 2013.

(30) Foreign Application Priority Data

Mar. 14, 2012  (JP) ................................. 2012-057569
Jul. 31, 2012  (JP) ................................. 2012-169498

(51) Int. Cl.
    *C07C 17/269* (2006.01)
    *C07C 17/25* (2006.01)

(52) U.S. Cl.
    CPC ............... *C07C 17/269* (2013.01); *C07C 17/25* (2013.01)

(58) Field of Classification Search
    CPC .............................. C07C 17/269; C07C 17/25
    USPC .......................................................... 570/159
    See application file for complete search history.

(56) References Cited

U.S. PATENT DOCUMENTS 2,931,840 A    4/1960   Marquis et al.

FOREIGN PATENT DOCUMENTS

| JP | 2007-535561 | 12/2007 |
| JP | 40-2132 | 2/2011 |
| JP | 5149456 | 12/2012 |

OTHER PUBLICATIONS

Yu et al, Chemosphere, 2007, 68(10), 2003-06.*
International Search Report issued Jun. 18, 2013 in PCT/JP2013/057258 filed Mar. 14, 2013.
U.S. Appl. No. 14/498,153, filed Sep. 26, 2014, Furuta, et al.
U.S. Appl. No. 14/486,125, filed Sep. 15, 2014, Furuta, et al.

* cited by examiner

*Primary Examiner* — Shailendra Kumar
(74) *Attorney, Agent, or Firm* — Oblon, McClelland, Maier & Neustadt, L.L.P.

(57) ABSTRACT

To provide an economically advantageous process for producing HFO-1234yf useful as a new refrigerant in sufficiently high yield by one reaction involving thermal decomposition. A process for producing HFO-1234yf and VdF from raw material containing R22, R40 and TFE, by a synthetic reaction involving thermal decomposition, which comprises (a) a step of supplying the R22, the R40 and the TFE to a reactor, as preliminarily mixed or separately, (b) a step of supplying a heat medium to the reactor, and (c) a step of bringing the heat medium in contact with the R22, the R40 and the TFE in the reactor to form the HFO-1234yf and the VdF.

15 Claims, 2 Drawing Sheets

Fig. 1

Fig. 2

PROCESS FOR PRODUCING 2, 3, 3, 3-TETRAFLUOROPROPENE AND 1, 1-DIFLUOROETHYLENE

This application is a CON of PCT/JP2013/057258, filed Mar. 14, 2013.

TECHNICAL FIELD

The present invention relates to a process for producing 2,3,3,3-tetrafluoropropene and 1,1-difluoroethylene, particularly to a process for producing 2,3,3,3-tetrafluoropropene and 1,1-difluoroethylene by one reaction from raw material comprising chlorodifluoromethane, chloromethane and tetrafluoroethylene.

BACKGROUND ART

In recent years, 2,3,3,3-tetrafluoropropene (HFO-1234yf) has attracted attention as a new refrigerant to replace 1,1,1,2-tetrafluoroethane (HFC-134a) which is a greenhouse gas. In this specification, with respect to a halogenated hydrocarbon, after its chemical name, an abbreviated name of the compound is shown in brackets, and in this specification, as the case requires, instead of the chemical name, its abbreviated name is used.

As a process for producing HFO-1234yf, for example, a process is known wherein 1,1-dichloro-2,2,3,3,3-pentafluoropropane (HCFC-225ca) is subjected to dehydrofluorination with an aqueous alkaline solution in the presence of a phase-transfer catalyst to obtain 1,1-dichloro-2,3,3,3-tetrafluoropropene (CFO-1214ya), which is then used as synthetic raw material and reduced by hydrogen to obtain HFO-1234yf.

However, this process has problems such that it requires multistage reactions whereby installation costs tend to be high, and distillation/purification of the intermediate product and the final product is difficult.

On the other hand, Patent Document 1 discloses that different types of hydrochlorocarbon compounds (e.g. chloromethane and chlorodifluoromethane) are combined and heated at 845±5° C. in the presence of steam for dehydrochlorination and condensation, whereby fluorinated olefins such as HFO-1234yf are formed.

Further, Patent Document 2 discloses a method for obtaining HFO-1234yf by heating and decomposing a mixture of chloromethane and tetrafluoroethylene (TFE) or chlorodifluoromethane at a temperature of from 700 to 950° C. by a common heating means such as an electric heater in a reactor.

However, in each of the methods disclosed in Patent Documents 1 and 2, although HFO-1234yf was formed by one reaction, it was not possible to obtain highly pure HFO-1234yf in sufficiently high yield, since the amount of a byproduct formed such as chlorotrifluoroethylene (CTFE) which is difficult to separate by distillation from HFO-1234yf, tended to be large.

Further, in the method disclosed in Patent Document 2, as the retention time increased, formation of high boiling products as by-products and carbonization of raw material were likely to occur whereby the reactor was likely to get blocked. Further, by the influence of an acid component formed as a byproduct, a special corrosion resistant apparatus (such as a reaction tube lined with platinum) was required, and thus, in consideration of the industrial production, such a method was totally unrealistic.

PRIOR ART DOCUMENTS

Patent Documents

Patent Document 1: JP-B-40-2132 (Example 4)
Patent Document 2: U.S. Pat. No. 2,931,840

DISCLOSURE OF INVENTION

Technical Problem

The present invention has been made in view of the above situations, and has an object to provide an economically advantageous process for producing HFO-1234yf useful as a new refrigerant in sufficiently high yield by one reaction involving thermal decomposition, by using readily available raw material. Further, it has an object to provide a process to obtain highly pure HFO-1234yf by preventing formation of CTFE as a byproduct which is difficult to separate by distillation from HFO-1234yf.

Solution to Problem

The present invention provides a process for producing 2,3,3,3-tetrafluoropropene (HFO-1234yf) and 1,1-difluoroethylene (VdF) from chlorodifluoromethane (R22), chloromethane (R40) and tetrafluoroethylene (TFE), which comprises (a) a step of supplying the R22, the R40 and the TFE to a reactor, as preliminarily mixed or separately,
(b) a step of supplying a heat medium to the reactor, and
(c) a step of bringing the heat medium in contact with the R22, the R40 and the TFE in the reactor to form the HFO-1234yf and the VdF.

Advantageous Effects of Invention

According to the process of the present invention, it is possible to produce HFO-1234yf useful as a new refrigerant in sufficiently high yield by using readily available R22, R40 and TFE as raw material and reacting them as they are without taking out an intermediate product from the reaction system. Accordingly, as compared with conventional methods for producing HFO-1234yf, it is possible to substantially reduce costs required for the raw material and production facilities.

Further, it is possible to prevent formation of a byproduct such as CTFE which is difficult to separate by distillation from HFO-1234yf, whereby it is possible to obtain highly pure HFO-1234yf. Further, it is possible to produce, together with HFO-1234yf, 1,1-difluoroethylene (VdF) which is useful as raw material for polyvinylidene fluoride to be used as material for water-treatment filters, various production machine components, etc., whereby economical merits are substantial. Furthermore, recycling of byproduct TFE is possible, whereby economical effects are substantial.

DESCRIPTION OF EMBODIMENTS

Now, embodiments of the present invention will be described.

The present invention provides a process for producing HFO-1234yf and VdF by a synthetic reaction involving thermal decomposition by using chlorodifluoromethane (R22), chloromethane (R40) and tetrafluoroethylene (TFE), as raw material. And, this process comprises (a) a step of supplying the R22, the R40 and the TFE to a reactor, as preliminarily mixed or separately, (b) a step of supplying a heat medium to the reactor, and (c) a step of bringing the heat medium in contact with the R22, the R40 and the TFE in the reactor to form the HFO-1234yf and the VdF.

The process of the present invention may be a continuous system process or a batch system process. In the continuous system process, the supply of R22, R40 and TFE as raw material to the reactor, the supply of the heat medium to the reactor and the withdrawal of the reaction mixture containing HFO-1234yf and VdF from the reactor are continuously conducted, respectively. In the batch system production, either one of the supply of the raw material in the step (a) and the supply of a heat medium in the step (b) may precede the other, or they may be conducted simultaneously. That is, even in a case where at the time of supplying either one of the raw material and the heat medium first, the other is not supplied to the reactor, the component to be supplied later may be supplied during the retention of the raw material or the heat medium supplied first, so that the raw material and the heat medium will be contacted with each other for a predetermined time in the reactor.

From the viewpoint of the production efficiency, the process of the present invention is preferably a continuous system process. In the following, the process of the present invention will be described with reference to an embodiment wherein it is applied to a continuous system production, but it should be understood that the present invention is by no means limited thereto.

Further, a step of withdrawing a reaction mixture containing HFO-1234yf and VdF from the reactor will hereinafter be referred to as the step (d). Therefore, in the continuous process, the steps (a), (b) and (d) are all conducted simultaneously.

<Reaction to Form HFO-1234yf>

In the present invention, a synthetic reaction involving thermal decomposition and dehydrochlorination as shown in the following formula (1) takes place to form HFO-1234yf and VdF.

It is considered that R22, R40 and TFE as raw material undergo a thermal decomposition and dehydrochlorination reaction to form a mixture containing difluorocarbene (F2C:), TFE and R40, and further, they are converted, directly by an addition reaction or via at least one type of intermediate, to tetrafluoropropene (particularly to HFO-1234yf) and VdF. In this invention, from such a thermal decomposition reaction to the reaction to form HFO-1234yf and VdF will be referred to as a synthetic reaction involving thermal decomposition.

Also in the case of a two component system using R22 and R40 and not using TFE as raw material, by the contact with a heat medium, a similar thermal decomposition/dehydrochlorination reaction takes place to form HFO-1234yf. However, in the present invention using a three component system raw material comprising R22, R40 and TFE, as compared with the case using the two component system raw material, the contact time of the raw material and the heat medium in the reactor can be shortened. Further, it is possible to prevent formation of byproducts and to obtain highly pure HFO-1234yf. These effects will be described in detail later.

Further, by using the three component system raw material comprising R22, R40 and TFE, the proportion of HFO-1234yf in the obtainable reaction mixture can be made high as a relative proportion to CTFE which is difficult to separate by distillation particularly from HFO-1234yf. Specifically, the ratio (molar ratio) in content proportion of HFO-1234yf to CTFE in the reaction mixture can be made to be at least 9.0 as the molar amount of HFO-1234yf/the molar amount of CTFE (hereinafter represented by "HFO-1234yf/CTFE"). HFO-1234yf/CTFE is preferably at least 10.0, more preferably at least 15.0. When the value of HFO-1234yf/CTFE is at least 9.0, the economical superiority is substantial as the process for producing HFO-1234yf.

Further, the present invention has a merit in that handling of the raw material can be conducted safely.

<Raw Material>

In the production of HFO-1234yf of the present invention, R22, R40 and TFE are used as raw material. The raw material may contain, in addition to such three components, compounds capable of forming difluorocarbene ($F_2C$:) when decomposed by contact with the heat medium in the reactor, e.g. hexafluoropropene (hereinafter referred to as HFP), CTFE, trifluoroethylene, octafluorocyclobutane (hereinafter referred to as RC318), hexafluoropropene oxide, etc.

Hereinafter, fluorinated compounds capable of forming F2C: by thermal decomposition in the reactor, other than R22 and TFE, will be referred to as "HFP, etc."

The molar ratio of the supply amount of TFE as one of the raw material components to the supply amount of R22 (hereinafter represented by TFE/R22), is made to be preferably within a range of from 0.01 to 100, more preferably within a range of from 0.1 to 10, particularly preferably within a range of from 0.1 to 3. Here, in this embodiment wherein the raw material and the heat medium are permitted to continuously flow in the reactor for the reaction, the supply amounts of the respective components of the raw material and the heat medium are deemed to represent the supply amounts per unit time. By adjusting the molar ratio TFE/R22 to be at least 0.1, it is possible not only to shorten the contact time with the heat medium, but also to obtain highly pure HFO-1234yf by preventing formation of byproducts. Further, by adjusting the molar ratio TFE/R22 to be at most 10, it is possible to obtain HFO-1234yf in higher yield. The molar ratio TFE/R22 is particularly preferably within a range of from 0.1 to 3.

Further, the molar ratio of the supply amount of R40 to the total of the supply amount of R22 and the supply amount of TFE (hereinafter represented by R40/(R22+TFE)) is made to be preferably within a range of from 0.01 to 100, more preferably within a range of from 0.1 to 10, particularly preferably within a range of from 0.33 to 3. By adjusting the molar ratio R40/(R22+TFE) to be from 0.01 to 100, it is possible to increase the conversion of R40 and to produce HFO-1234yf in high yield.

The temperature of R22 to be supplied to the reactor and the temperature of HFP, etc. to be supplied to the reactor, are preferably made to be from 0 to 600° C. with a view to adjusting them to a temperature where carbonization hardly takes place while the reactivity is high to a certain extent.

From the viewpoint of further improving the reactivity, it is preferred to heat R22 and HFP, etc. to at least ordinary temperature (25° C.) and at most 600° C., or more preferred to heat them from 100 to 500° C., before introducing them to the reactor.

Whereas, the temperature of R40 to be supplied to the reactor is preferably made to be from 0 to 1,200° C. from the viewpoint of the reactivity. With a view to further improving the reactivity, it is preferred to heat R40 to at least ordinary temperature (25° C.) and at most 1,200° C., or more preferred to heat it from 100 to 800° C., before introducing it to the reactor.

The temperature of TFE to be supplied to the reactor is preferably made to be from 0 to 1,200° C. from the viewpoint of the reactivity. With a view to further improving the reactivity, it is preferred to heat TFE to at least ordinary temperature (25° C.) and at most 1,200° C., or more preferred to heat it from 100 to 800° C., before introducing it to the reactor.

The respective raw material components such as R22, R20 and TFE and further HFP, etc. which are used as the case requires, may be supplied to the reactor separately, or the respective components may be mixed and then supplied to the reactor. In a case where the respective components are mixed and then supplied, the raw material components may be divided into groups, e.g. into a group of fluorinated compounds capable of forming F2C: and another group of others, and the respective groups may be mixed and then separately supplied to the reactor, or all raw material components may be mixed and then supplied. When the above-mentioned difference in the supply temperature is taken into consideration, it is preferred that R22, TFE and HFP, etc. to be used as the case requires, are mixed, adjusted to the above-mentioned preferred temperature and then supplied to the reactor, and separately therefrom, R40 is adjusted to the above-mentioned preferred temperature and then supplied to the reactor.

Whereas, in a case where the respective raw material components such as R22, R40 and TFE and further, HFP, etc. to be used as the case requires, are preliminarily mixed and then supplied to the reactor, with a view to preventing the reaction/decomposition from proceeding before the reactor, the temperature at the time of introduction to the reactor is adjusted to be preferably lower than 600° C., particularly preferably lower than 500° C.

<Heat Medium>

The heat medium in the present invention is supplied to the reactor so that it will be in contact with the above-mentioned raw material for a certain time in the reactor. The heat medium is a medium which undergoes no thermal decomposition at the temperature in the reactor, and specifically, it is preferably a medium which undergoes no thermal decomposition at a temperature of from 100 to 1,200° C. The heat medium may be at least one member selected from steam, nitrogen and carbon dioxide. It is preferred to use a gas containing steam in an amount of at least 50 vol % and the rest being nitrogen and/or carbon dioxide. In order to remove HCl formed by a thermal decomposition reaction of the above formula (1) in the form of hydrochloric acid, the content ratio of steam in the heat medium is preferably at least 50 vol %, and it is particularly preferred to use a gas consisting substantially solely of steam (100 vol %).

The supply amount of the heat medium is preferably a proportion of from 20 to 98 vol %, more preferably from 50 to 95 vol %, in the total of the supply amounts of the heat medium and the raw material. By adjusting the proportion of the supply amount of the heat medium to be at least 20 vol % to the total of the supply amounts of the heat medium and the raw material, it becomes possible to produce HFO-1234yf and VdF in sufficiently high yield by facilitating the thermal decomposition reaction of the above formula (1) while preventing formation of high-boiling point products or carbonization of the raw material. Whereas, if the proportion exceeds 98 vol %, the productivity lowers substantially, such being industrially not practical.

Further, from the viewpoint of the thermal decomposition and the reactivity of the raw material components, the temperature of the heat medium to be supplied to the reactor is adjusted to be preferably from 100 to 1,200° C. With a view to further improving the reactivity of the raw material components, the temperature of the heat medium to be supplied to the reactor is adjusted to be more preferably from 600 to 900° C., particularly preferably from 700 to 900° C.

The contact time in the reactor, of the heat medium and the raw material thus supplied, is adjusted to be preferably from 0.01 to 10 seconds, more preferably from 0.2 to 3.0 seconds. By adjusting the contact time to be from 0.01 to 10 seconds, it is possible to sufficiently facilitate the reaction to form HFO-1234yf and to prevent formation of byproducts. Here, the contact time of the heat medium and the raw material corresponds to the retention time of the raw material in the reactor and can be controlled by adjusting the supply amount (flow rate) of the raw material to the reactor.

<Reactor>

As the reactor, so long as it is one durable to the aftermentioned temperature and pressure in the reactor, its shape is not particularly limited, and for example, a cylindrical vertical reactor may be mentioned. The material for the reactor may, for example, be glass, iron, nickel or an alloy containing iron and nickel as the main components.

The temperature in the reactor in the step (c) is set to be a temperature of at least the temperature of R22, R40 and TFE as the raw material to be supplied to the reactor, and preferably from 400 to 1,200° C., further preferably within a range of from 600 to 900° C., particularly preferably within a range of from 710 to 900° C. By adjusting the temperature in the reactor to be within the range of from 400 to 1,200° C., it is possible to increase the reaction rate of the formation reaction involving thermal decomposition represented by the above formula (1) and to obtain HFO-1234yf, etc. in sufficiently high yield.

The temperature in the reactor can be controlled by adjusting the temperature and pressure of the above heat medium to be supplied to the reactor. Further, it is also possible to supplementarily heat the inside of the reactor by e.g. an electric heater so that the temperature in the reactor becomes to be within the particularly preferred temperature range (from 710 to 900° C.).

The pressure in the reactor is adjusted to be preferably from 0 to 2.0 MPa, more preferably within a range of from 0 to 0.5 MPa, by gauge pressure.

<Reaction Apparatus>

Figure 1:
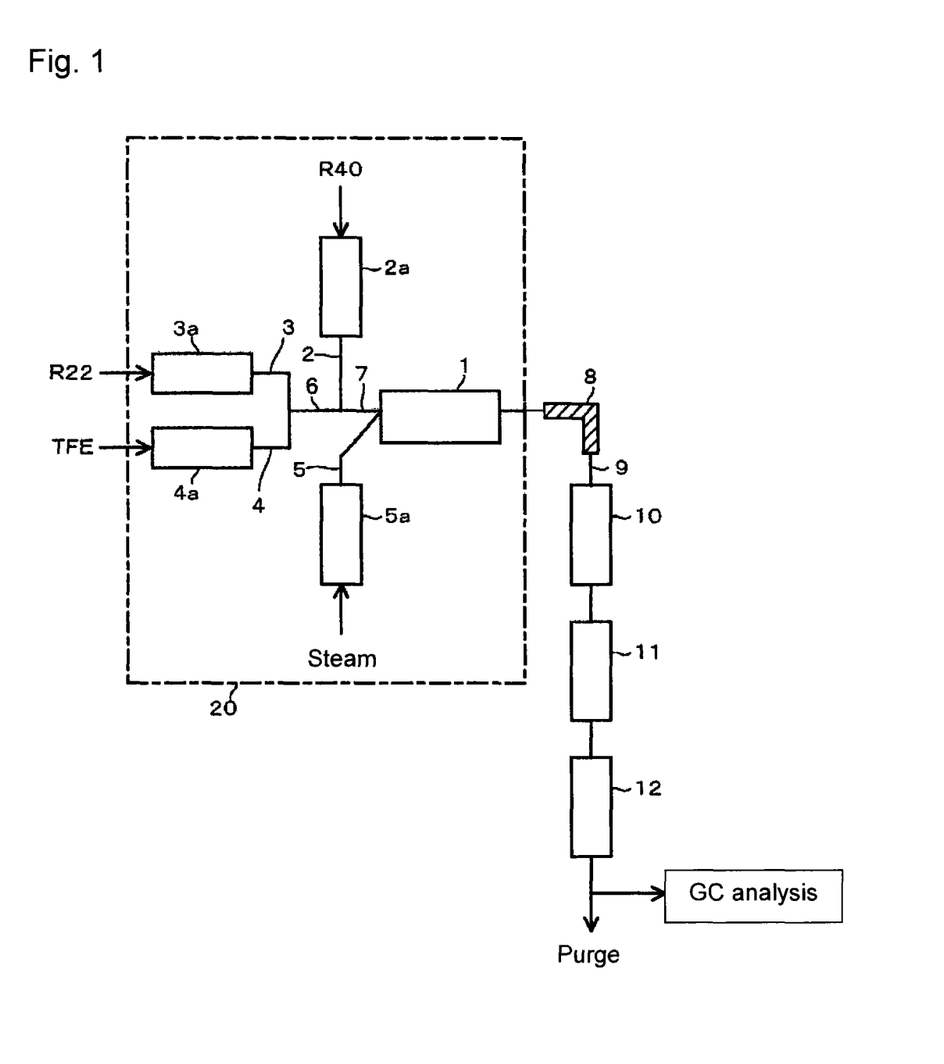
FIG. 1 is a view illustrating an example of a reaction apparatus to be used for the process of the present invention.
Figure 2:
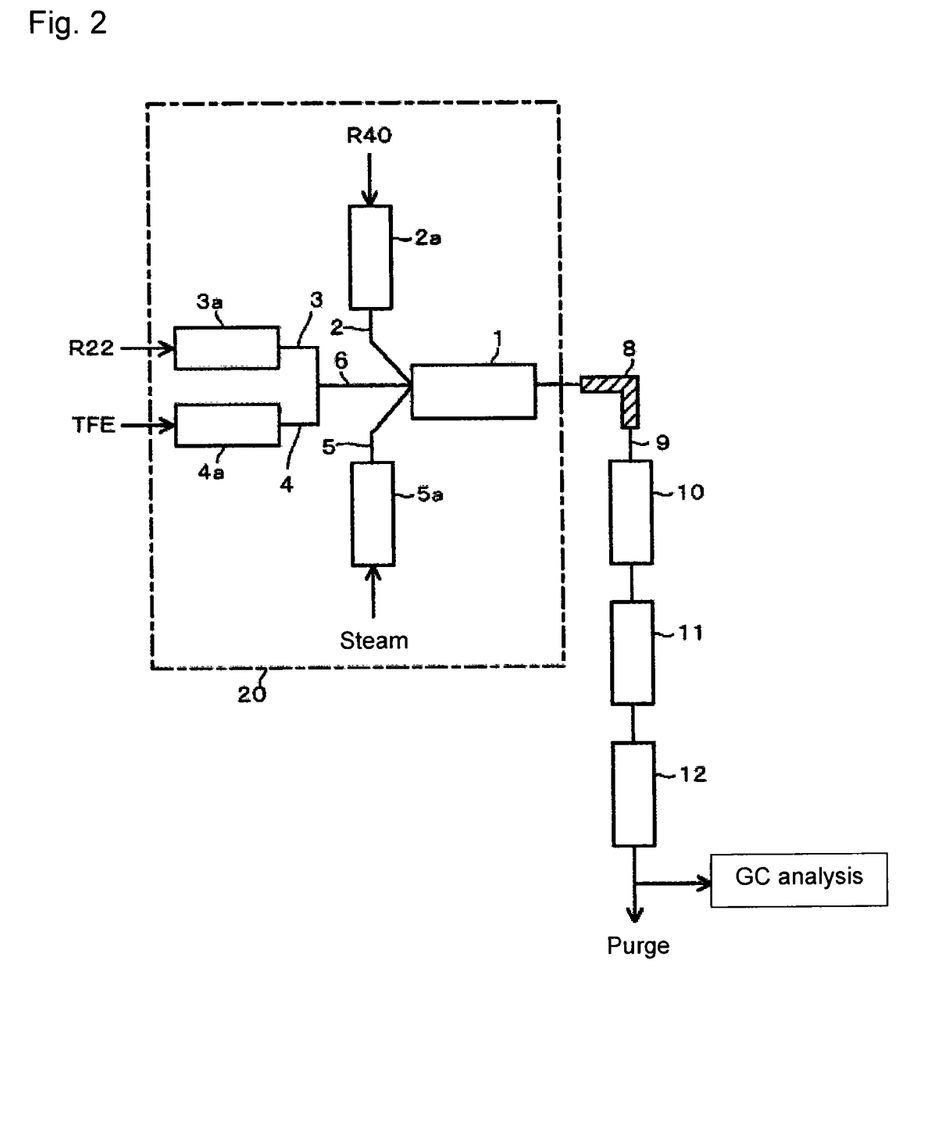
FIG. 2 is a view illustrating another example of a reaction apparatus to be used for the process of the present invention.

Examples of the reaction apparatus to be used for the production of HFO-1234yf, etc. in the present invention are shown in FIGS. 1 and 2.

The reaction apparatus 20 has a reactor 1 provided with a heating means such as an electric heater. To the reactor 1, a supply line 2 for R40 as a first raw material component, a supply line 3 for R22 as a second raw material component, a supply line 4 for TFE as a third raw material component and a supply line 5 for steam, are connected as described in the following. Here, provision of the heating means in the reactor 1 is not necessarily required.

The supply line 2 for R40, the supply line 3 for R22 and the supply line 4 for TFE, are, respectively, provided with preheaters 2a, 3a and 4a each provided with an electric heater or the like, so that the respective raw material components to be supplied, are preheated to predetermined temperatures and then supplied to the reactor 1. Further, the supply line 5 for steam, is provided with a superheated steam generator 5a, whereby the temperature and pressure of steam to be supplied, are adjusted. Here, provision of preheaters 2a, 3a and 4a is not necessarily required.

These supply lines 2, 3 and 4 may be separately connected to the reactor 1, respectively, but as shown in FIG. 2, a R22 and TFE raw material supply line 6 having a raw material supply line 3 and a raw material supply line 4 interlinked, may be connected to the reactor 1. Otherwise, for example, as shown in FIG. 1, the supply line 3 for R22 and the supply line 4 for TFE may be interlinked after the respective preheaters 3a and 4a, and to this interlinked R22 and TFE raw material supply line 6, the supply line 2 for R40 after the preheater 2a may be further linked. That is, the construction may be such that the preheated R22 and TFE are mixed, and then, to this raw material mixture of R22 and TFE, the preheated R40 is further mixed, so that the raw material mixture having all raw material components mixed, will be supplied to the reactor 1 from the raw material mixture-supply line 7.

On the other hand, steam may be mixed with a part or all of the raw material and then supplied to the reactor 1, but it is preferred to supply it to the reactor separately from the raw material. That is, as shown in FIGS. 1 and 2, it is preferred that steam is supplied to the reactor 1 from a steam-supply line 5 separately from the raw material mixture.

To the outlet of the reactor 1, an outlet line 9 having a cooling means 8 such as a heat exchanger installed, is connected. In the outlet line 7, further, a steam and acidic liquid-recovery tank 10, an alkaline cleaning device 11 and a dehydrating tower 12 are sequentially installed. And, it is so designed that after dehydration by the dehydrating tower 12, the respective components in the obtained gas are analyzed and quantified by an analytical device such as gas chromatography (GC).

Here, a gas obtained by withdrawing the reaction mixture containing HFO-1234yf and TFE from the reactor 1 and removing an acidic substance such as hydrogen chloride, steam, water, etc. by the above-mentioned treatments in the outlet line 9, will be hereinafter referred to as outlet gas.

<Outlet Gas Components>

In the process of the present invention, HFO-1234yf and VdF are obtainable as components of the above outlet gas. Compounds other than HFO-1234yf and VdF contained in the outlet gas may, for example, be methane, ethylene, TFE, HFP, CTFE, trifluoroethylene, RC318, 3,3,3-trifluoropropene (CF3CH=CH2; HFO-1243zf), etc. Among these components, methane and ethylene having a methylene group (=CH2) or a methyl group (—CH3) are compounds derived from raw material component R40, and TFE, HFP, CTFE, trifluoroethylene, RC318 and HFO-1243zf having fluorine atoms are, respectively, compounds derived from R22 and/or TFE among the raw material components. Further, HFO-1234yf and VdF are compounds derived from R22 and/or TFE and also compounds derived from R40.

The above components other than HFO-1234yf and VdF contained in the outlet gas can be removed to a desired extent by a known means such as distillation, etc. And, separated TFE may be recycled as a part of raw material, Further, HFP, CTFE, trifluoroethylene and RC318 are also compounds capable of forming difluorocarbene ($F_2C$:) and may be recycled as a part of raw material. Here, CTFE contained as a byproduct in the outlet gas is difficult to separate by distillation from HFO-1234yf since the boiling point is close, but the proportion of the amount of byproduct CTFE to the formed amount of HFO-1234yf is low, and therefore, it is possible to obtain highly pure HFO-1234yf by distillation for purification.

According to the process of the present invention, it is possible to produce HFO-1234yf useful as a new refrigerant in sufficiently high yield with a global warming potential (GWP) being as small as 4, by one reaction using R22, R40 and TFE as raw material. For example, according to the process of the present invention, as compared with conventional methods for producing HFO-1234yf, it is possible not only to reduce costs required for the raw material and production facilities but also to substantially reduce the energy required for the production. Further, it is possible to produce, together with HFO-1234yf, VdF which is useful as raw material for polyvinylidene fluoride which is industrially used for e.g. a water-treating filter, and thus, it is possible to produce a material important for maintaining the global environment at low costs with a low energy and simultaneously.

Also in the case of a two component system using R22 and R40 and not using TFE as raw material, by the contact with a heat medium, a similar thermal decomposition/dehydrochlorination reaction takes place to form HFO-1234yf and VdF. However, in the present invention using a three component system raw material comprising R22, R40 and TFE, as compared with the case using the two component system raw material, the contact time of the raw material and the heat medium in the reactor can be shortened.

Further, in the present invention, it is possible to obtain highly pure HFO-1234yf by preventing formation of a byproduct which is very difficult to separate since the boiling point is close among byproducts derived from R22 and TFE. That is, among byproducts derived from R22 and TFE, CTFE has a boiling point of −28° C. which is very close to the boiling point (−29° C.) of HFO-1234yf and is difficult to separate or purify by common separation/purification techniques (such as distillation, etc.), but in the present invention, by using the three component system raw material comprising R22, R40 and TFE, the proportion of the amount of CTFE formed to the amount of HFO-1234yf formed can be substantially reduced, and it is possible to obtain HFO-1234yf having a higher purity.

EXAMPLES

Now, the present invention will be described in further detail with reference to Examples, but it should be understood that the present invention is by no means restricted by these Examples.

Example 1

Using the reaction apparatus as shown in FIG. 1, from a raw material gas comprising R22, R40 and TFE, crude HFO-1234yf and crude VdF were obtained as follows.

Into a stainless steel tube in an electric furnace set at an internal temperature of 300° C., R40 was continuously introduced, and R40 was heated (preheated) to 300° C. Further, into a stainless steel tube in an electric furnace set at an internal temperature of 300° C., R22 was continuously introduced, and R22 was preheated to 300° C. Furthermore, into a stainless steel tube in an electric furnace set at an internal temperature of 300° C., TFE was continuously introduced, and TFE was preheated to 300° C.

These preheated raw material gas components (R40, R22 and TFE) and steam (water vapor) heated by an electric furnace set at an internal temperature of 750° C. were supplied to a reactor controlled to have an internal pressure (gauge pressure) of 0.04 MPa and an internal temperature of 800° C., so that the molar ratios of the supply amounts of the raw material components would be TFE/R22=50/50(=1.0)(i.e. TFE/(TFE+R22)=50/100)

R40/(R22+TFE)=42.8/57.1=0.75, and the volume ratio of steam to the entire raw material gas supply amount would be steam/(R40+R22+TFE)=90/10(i.e. R40/R22/TFE/steam=4.3/2.8/2.8/90).

Here, the volume ratio of the supply amount of steam to the supply amount of the entire gas to be supplied to the reactor (hereinafter referred to as the flow volume ratio of steam) would be 90/(10+90)=0.9 (90%). Further, the molar ratio of R40 to the total of R22 and TFE is, as mentioned above, 0.75 (R40/(R22+TFE)=42.8/57.1), but from the viewpoint of the function as a compound containing fluorine atoms among the components constituting the raw material, 1 mol of TFE corresponds to 2 mol of R22 and can be counted as 2 equivalents, and thus, the equivalent ratio of R40 to R22 and TFE would be 0.5 from the following calculation.

R40/(R22+TFE)=42.8/(28.55+28.55×2)=0.5

Thus, the flow rate of the raw material gas (the supply amount per unit time) was controlled so that the retention time of the raw material gas in the reactor would be 0.5 second, and the gas of the reaction mixture was withdrawn from the outlet of the reactor. The measured value of the internal temperature of the reactor was 800° C., and the measured value of the internal pressure of the reactor was 0.042 MPa. Here, the gas of the reaction mixture withdrawn from the outlet of the reactor contains unreacted raw material gas in addition to the gas formed by the reaction or by side reactions.

Then, the gas of the reaction mixture withdrawn from the outlet of the reactor was cooled to at most 100° C. and subjected to recovery of steam and the acidic liquid and alkaline cleaning sequentially and then to dehydration treatment, whereupon the obtained outlet gas was analyzed by gas chromatography, and the molar composition of the gas components contained in the outlet gas was calculated. These results are shown in Table 1 together with the reaction conditions.

Here, the preheat temperatures of R40, R22 and TFE are preset temperatures in the respective electric furnaces for preheating, and the steam temperature is a preset temperature in the electric furnace for heating steam. Further, the steam pressure is a preset pressure.

Further, based on the molar composition of the outlet gas obtained by the analysis by gas chromatography, the conversion (reaction rate) of R40, the selectivity of each component derived from R40, the conversion (reaction rate) of R22 and TFE, the selectivity of each component derived from R22 and/or TFE, and the ratio of HFO-1234yf to CTFE (HFO-1234yf/CTFE) were, respectively, obtained. These results are shown in the lower columns in Table 1.

The above values have the following meanings, respectively.
(R40 Conversion (Reaction Rate))

When the proportion (R40 recovery rate) which R40 occupies among R40-derived components (i.e. components having a methylene group or a methyl group) in the outlet gas is X %, (100−X) % is referred to as the conversion (reaction rate) of R40. It means the proportion (mol %) of reacted R40.
(Selectivity of Each Component Derived from R40)

In reacted R40, % of one converted to each component other than R40. The selectivity of each component is obtainable by [yield of each component derived from R40]/[conversion (reaction rate) of R40]. Here, the yield of each component derived from R40 is the proportion (mol %) which each component other than R40 occupies among R40-derived components in the outlet gas.
(Conversion (Reaction Rate) of R22 and TFE)

When the proportion (R22 and/or TFE recovery rate) which R22 and/or TFE occupies among R22 and/or TFE-derived components being compounds containing fluorine atoms (components having fluorine atoms) in the outlet gas is X %, (100−X) % is referred to as the conversion (reaction rate) of R22 and/or TFE. It means the proportion (mol %) of reacted R22 and/or TFE.
(Selectivity of Each Component Derived from R22 and/or TFE)

In reacted R22 and/or TFE, % of one converted to each component other than R40. The selectivity of each component is obtainable by [yield of each component derived from R22 and/or TFE]/[conversion (reaction rate) of R22 and/or TFE]. Here, the yield of each component derived from R22 and/or TFE is the proportion (mol %) which each component other than R22 occupies among R22- and/or TFE-derived components in the outlet gas.

In Examples of the present invention wherein the raw material gas contains TFE, TFE undergoes a reaction or conversion, but it may have been formed from R22, and therefore, it is impossible to obtain the conversion (reaction rate) of only TFE. Likewise, it is impossible to determine whether HFO-1234yf or VdF being a product having fluorine atoms, is one formed from R22 or one formed from TFE. Therefore, on the assumption that "raw material TFE is all R22", the proportion in which such raw material R22 is reacted, is deemed to be the conversion (reaction rate) of R22 and/or TFE. Further, the percentage (%) of each component converted from such raw material R22 is obtained and taken as the selectivity of each component derived from R22 and/or TFE.
(HFO-1234yf/CTFE Ratio)

The proportion of HFO-1234yf present to CTFE present in the outlet gas. It is obtainable by [selectivity of HFO-1234yf derived from R22 and/or TFE]/[selectivity of CTFE derived from R22 and/or TFE]. It represents in what proportion (molar ratio), HFO-1234yf is present to CTFE in the outlet gas.

Examples 2 to 4

The molar ratio (TFE/(TFE+R22)) of the supply amount of TFE to the total supply amount of TFE and R22 was made to be 0.1 (10%) in Example 2, 3 (30%) in Example 3 and 0.7 (70%) in Example 4. Further, so that the equivalent ratio of R40/(TFE+R22) would be 0.5, the molar ratio of R40/(TFE+R22) was made to be 0.55 in Example 2, 0.65 in Example 3 and 0.85 in Example 4. Otherwise, the reaction was conducted under the same conditions as in Example 1.

Then, the gas of the reaction mixture withdrawn from the outlet of the reactor was cooled to at most 100° C. and subjected to recovery of steam and the acidic liquid and alkaline cleaning sequentially and then to dehydration treatment, whereupon the obtained outlet gas was analyzed by gas chromatography, and the molar composition of the gas components contained in the outlet gas was calculated. Further, based on the obtained molar composition of the outlet gas, the conversion (reaction rate) of R40, the selectivity of each component derived from R40, the conversion (reaction rate) of R22 and/or TFE, the selectivity of each component derived from R22 and/or TFE, and the ratio of HFO-1234yf to CTFE (HFO-1234yf/CTFE) were, respectively, obtained. These results are shown in the lower columns in Table 1.

Comparative Example 1

Using a raw material gas composed solely of R22 and R40 without using TFE as raw material gas, crude HFO-1234yf and crude VdF were obtained as follows.

Into a stainless steel tube in an electric furnace set at an internal temperature of 300° C., R40 was continuously introduced, and R40 was heated (preheated) to 300° C. Further, into a stainless steel tube in an electric furnace set at an internal temperature of 300° C., R22 was continuously introduced, and R22 was preheated to 300° C.

These preheated raw material gas components (R40 and R22) and steam heated by an electric furnace set at an internal temperature of 750° C. were supplied to a reactor controlled to have an internal pressure (gauge pressure) of 0.04 MPa and an internal temperature of 800° C., so that the molar ratios of the supply amounts of R40 and R22 would be R40/R22=33/67, and the volume ratio of the flow rate of steam to the supply amount of the raw material gas would be steam/(R40+R22)=90/10 (R40/R22/steam=3.3/6.7/90). Here, the volume ratio of the supply amount of steam to the supply amount of the entire gas to be supplied to the reactor (the flow volume ratio of steam) is 90 vol % in the same manner as in Example 1. And, the flow rate of the raw material gas was controlled so that the retention time of the raw material gas in the reactor would be 0.5 second, and the gas of the reaction mixture was withdrawn from the outlet of the reactor. The measured value of the internal temperature of the reactor was 800° C., and the measured value of the internal pressure of the reactor was 0.042 MPa.

Then, the gas of the reaction mixture withdrawn from the outlet of the reactor was cooled to at most 100° C. and subjected to recovery of steam and the acidic liquid and alkaline cleaning sequentially and then to dehydration treatment, whereupon the obtained outlet gas was analyzed by gas chromatography, and the molar composition of the gas components contained in the outlet gas was calculated. Based on the obtained molar composition of the outlet gas, the conversion (reaction rate) of R40, the selectivity of each component derived from R40, the conversion (reaction rate) of R22 and/or TFE, the selectivity of each component derived from R22 and/or TFE, and the ratio of HFO-1234yf to CTFE (HFO-1234yf/CTFE) were, respectively, obtained. The results are shown in the lower columns in Table 1.

Example 5

Without conducting preheating of R40, R22 and TFE, the respective raw material components at room temperature (10° C.) were supplied as they were, to the reactor. Otherwise, the reaction was conducted under the same conditions as in Example 1.

Then, the gas of the reaction mixture withdrawn from the outlet of the reactor was cooled to at most 100° C. and subjected to recovery of steam and the acidic liquid and alkaline cleaning sequentially and then to dehydration treatment, whereupon the obtained outlet gas was analyzed by gas chromatography, and the molar composition of the gas components contained in the outlet gas was calculated. Based on the obtained molar composition of the outlet gas, the conversion (reaction rate) of R40, the selectivity of each component derived from R40, the conversion (reaction rate) of R22 and/or TFE, the selectivity of each component derived from R22 and/or TFE, and the ratio of HFO-1234yf to CTFE (HFO-1234yf/CTFE) were, respectively, obtained. The results are shown in the lower columns in Table 1.

Comparative Example 2

A raw material composed solely of R22 and R40 was used without using TFE as raw material gas. And, without conducting preheating of R40 and R22, the respective raw material components at room temperature (10° C.) were supplied as they were, to the reactor. Otherwise, the reaction was conducted under the same conditions as in Example 1.

Then, the gas of the reaction mixture withdrawn from the outlet of the reactor was cooled to at most 100° C. and subjected to recovery of steam and the acidic liquid and alkaline cleaning sequentially and then to dehydration treatment, whereupon the obtained outlet gas was analyzed by gas chromatography, and the molar composition of the gas components contained in the outlet gas was calculated. Based on the obtained molar composition of the outlet gas, the conversion (reaction rate) of R40, the selectivity of each component derived from R40, the conversion (reaction rate) of R22 and/or TFE, the selectivity of each component derived from R22 and/or TFE, and the ratio of HFO-1234yf to CTFE (HFO-1234yf/CTFE) were, respectively, obtained. The results are shown in the lower columns in Table 1.

TABLE 1

|  | Ex. 1 | Ex. 2 | Ex. 3 | Ex. 4 | Ex. 5 | Comp. Ex. 1 | Comp. Ex. 2 |
| --- | --- | --- | --- | --- | --- | --- | --- |
| Temperature (° C.) in reactor | 800 | 800 | 800 | 800 | 800 | 800 | 800 |
| Pressure (MPa) in reactor | 0.042 | 0.042 | 0.042 | 0.042 | 0.042 | 0.042 | 0.042 |
| Retention time (s) | 0.5 | 0.5 | 0.5 | 0.5 | 0.5 | 0.5 | 0.5 |
| Equivalent ratio of R40/(R22 + TFE × 2) | 0.5 | 0.5 | 0.5 | 0.5 | 0.5 | 0.5 | 0.5 |
| Molar ratio of R40/(R22 + TFE) | 0.75 | 0.55 | 0.65 | 0.85 | 0.75 | 0.5 | 0.5 |
| Molar ratio of TFE/(R22 + TFE) | 0.5 | 0.1 | 0.3 | 0.7 | 0.5 | 0 | 0 |
| Molar ratio of TFE/R22 | 1.00 | 0.11 | 0.43 | 2.33 | 1.00 | 0 | 0 |
| R40-preheat temperature (° C.) | 300 | 300 | 300 | 300 | 10 | 300 | 10 |
| R22, TFE-preheat temperature (° C.) | 300 | 300 | 300 | 300 | 10 | 300 | 10 |
| Steam flow volume ratio (%) | 90 | 90 | 90 | 90 | 90 | 90 | 90 |
| Steam temperature (° C.) | 750 | 750 | 750 | 750 | 750 | 750 | 750 |
| Steam pressure (MPaG) | 0.042 | 0.042 | 0.042 | 0.042 | 0.042 | 0.042 | 0.042 |
| R40 conversion (=R40 reaction rate (%)) | 47.81 | 50.50 | 49.47 | 43.14 | 49.70 | 48.71 | 49.03 |

TABLE 1-continued

|  |  | Ex. 1 | Ex. 2 | Ex. 3 | Ex. 4 | Ex. 5 | Comp. Ex. 1 | Comp. Ex. 2 |
|---|---|---|---|---|---|---|---|---|
| Selectivity (%) of R40-derived components | 1234yf | 22.6 | 21.5 | 22.4 | 24.0 | 22.3 | 22.0 | 21.5 |
|  | VdF | 73.1 | 73.3 | 73.2 | 71.3 | 73.7 | 74.4 | 74.3 |
|  | Others | 4.3 | 5.2 | 4.4 | 4.7 | 4.0 | 3.6 | 4.2 |
| R22 and TFE-conversion (%) |  | 96.22 | 95.37 | 95.82 | 97.67 | 96.83 | 93.05 | 94.30 |
| Selectivity (%) of R22 and/or TFE-derived components | TFE | 59.77 | 61.14 | 59.63 | 67.03 | 59.94 | 62.31 | 63.38 |
|  | 1234yf | 11.40 | 10.46 | 11.43 | 9.09 | 11.18 | 10.44 | 9.86 |
|  | VdF | 18.41 | 17.85 | 18.66 | 13.50 | 18.51 | 17.66 | 17.06 |
|  | CTFE | 0.60 | 1.01 | 0.79 | 0.32 | 0.63 | 1.19 | 1.17 |
|  | Others | 9.82 | 9.54 | 9.48 | 10.05 | 9.73 | 8.39 | 8.53 |
| 1234yf/CTFE ratio |  | 19.14 | 10.37 | 14.41 | 28.01 | 17.78 | 8.74 | 8.45 |

As is evident from Table 1, in Examples 1 to 5, formation of CTFE which is very difficult to separate as the boiling point is close to HFO-1234yf, among products derived from R22 and/or TFE, is prevented, and it is possible to obtain highly pure HFO-1234yf.

That is, in Example 1 wherein the molar ratio of TFE to TFE+R22 is 50%, 86.2% in the components derived from R22 and/or TFE in the outlet gas, was HFO-1234yf and VdF as desired products and TFE as one of raw material components, and the respective formed molar ratios were HFO-1234yf/VdF/TFE=10.6/34.0/55.3. And, the total in selectivity of HFO-234yf and VdF based on R40 was 95.7% (22.6%+73.1%), and the formed molar ratio of HFO-1234yf to CTFE (HFO-1234yf/CTFE) was as large as 19.14.

Whereas, in Comparative Example 1 wherein a raw material composed of R40 and R22 was used without using TFE, the yield in total of HFO-1234yf and VdF as the desired products and TFE as one of the raw material components, was 84.1% which is lower than in Example 1, and the respective formed molar ratios were HFO-1234yf/VdF/TFE=9.7/332.7/57.7, i.e. each of the formed molar ratios of HFO-1234 and VdF is lower than in Example 1. And, the total in selectivity of HFO-1234yf and VdF based on R40 was 96.4% (22.0%+74.4%), which is slightly higher than in Example 1, but the formed molar ratio of HFO-1234yf to CTFE (HFO-1234yf/CTFE) was 8.74, which is substantially low as compared with Example 1.

Thus, it is evident that in Example 1, as compared with Comparative Example 1, formation of CTFE to formation of HFO-1234yf is suppressed, and HFO-1234 having a higher purity is obtained. It is further evident that also in Examples 2 to 5, as compared with Comparative Examples 1 and 2, formation of CTFE to formation of HFO-1234yf is suppressed, whereby HFO-1234yf/CTFE is higher, and HFO-1234 having a higher purity is obtained.

Further, it is evident that even when the molar ratio of TFE in the raw material gas is increased from 0% (Comparative Example 1) to 10% (Example 2), 30% (Example 3) or 50% (Example 1), the proportion (molar ratio) of TFE in the outlet gas will not increase and rather tends to decrease, and the ratio of TFE to HFO-1234yf decreases, which indicates an increase of formation of HFO-1234yf as compared with TFE. This indicates that the use of TFE as a raw material component is effective for the formation of HFO-1234yf.

Furthermore, the following is evident from Table 1. That is, when TFE is used as a part of raw material so that the molar ratio of TFE in TFE+R22 (i.e. TFE/(TFE+R22)) becomes at least 10%, irrespective of preheating, the yield of HFO-1234yf in the outlet gas increases, and particularly, the selectivity of HFO-1234yf derived from R22 and/or TFE increases substantially. Thus, it is evident that the use of TFE as a part of raw material is effective for selectively obtaining HFO-1234yf.

Examples 6 to 9

In Examples 6 to 8, the reaction was conducted under the same conditions as in Example 1 except that the temperature in the reactor was changed as shown in Table 2. Further, in Example 9, the reaction was conducted under the same conditions as in Example 1 except that using the reaction apparatus as shown in FIG. 2, the preheat temperature of R40 was changed as shown in Table 2. Then, the gas of a reaction mixture withdrawn from the outlet of the reactor was treated in the same manner as in Example 1, and then, the obtained outlet gas was analyzed in the same manner as in Example 1. The results are shown in Table 2 together with the reaction conditions.

TABLE 2

|  |  | Ex. 6 | Ex. 7 | Ex. 8 | Ex. 9 |
|---|---|---|---|---|---|
| Temperature (° C.) in reactor |  | 730 | 770 | 850 | 800 |
| Pressure (MPa) in reactor |  | 0.042 | 0.042 | 0.042 | 0.042 |
| Retention time (s) |  | 0.5 | 0.5 | 0.5 | 0.5 |
| Equivalent ratio of R40/(R22 + TFE × 2) |  | 0.5 | 0.5 | 0.5 | 0.5 |
| Molar ratio of R40/(R22 + TFE) |  | 0.75 | 0.75 | 0.75 | 0.75 |
| Molar ratio of TFE/(R22 + TFE) |  | 0.5 | 0.5 | 0.5 | 0.5 |
| Molar ratio of TFE/R22 |  | 1.00 | 1.00 | 1.00 | 1.00 |
| R40-preheat temperature (° C.) |  | 300 | 300 | 300 | 700 |
| R22, TFE-preheat temperature (° C.) |  | 300 | 300 | 300 | 300 |
| Steam flow volume ratio (%) |  | 90 | 90 | 90 | 90 |
| Steam temperature (° C.) |  | 750 | 750 | 750 | 750 |
| Steam pressure (MPaG) |  | 0.042 | 0.042 | 0.042 | 0.042 |
| R40 conversion (=R40 reaction rate (%)) |  | 10.97 | 27.25 | 73.13 | 53.15 |
| Selectivity (%) of R40-derived components | 1234yf | 36.2 | 29.2 | 13.2 | 22.2 |
|  | VdF | 62.7 | 67.8 | 82.8 | 72.7 |
|  | Others | 1.1 | 3.0 | 4.0 | 5.1 |
| R22 and TFE-conversion (%) |  | 96.47 | 96.84 | 98.09 | 95.64 |
| Selectivity (%) of R22 and/or TFE-derived components | TFE | 86.47 | 71.16 | 11.98 | 57.94 |
|  | 1234yf | 3.88 | 10.49 | 17.11 | 11.69 |
|  | VdF | 3.36 | 10.54 | 53.54 | 19.16 |
|  | CTFE | 0.09 | 0.28 | 1.03 | 0.65 |
|  | Others | 6.20 | 7.53 | 11.35 | 10.56 |
| 1234yf/CTFE ratio |  | 44.21 | 38.30 | 16.59 | 18.18 |

INDUSTRIAL APPLICABILITY

According to the process of the present invention, it is possible to produce HFO-1234yf useful as a new refrigerant in sufficiently high yield by one reaction, using readily available R22, R40 and TFE as raw material, and as compared with conventional methods for producing HFO-1234yf, it is possible to reduce costs required for the raw material and production facilities.

Further, it is possible to prevent formation of a byproduct such as CTFE which is difficult to separate by distillation from HFO-1234yf and to obtain HFO-1234yf in sufficiently high yield. Further, it is possible to produce, together with HFO-1234yf, VdF which is useful as raw material for e.g. polyvinylidene fluoride, and thus, economical merits are substantial.

This application is a continuation of PCT Application No. PCT/JP2013/057258, filed on Mar. 14, 2013, which is based upon and claims the benefit of priority from Japanese Patent Application No. 2012-057569 filed on Mar. 14, 2012 and Japanese Patent Application No. 2012-169498 filed on Jul. 31, 2012. The contents of those applications are incorporated herein by reference in their entireties.

REFERENCE SYMBOLS

1: reactor, 2: supply line for R40, 3: supply line for R22, 4: supply line for TFE, 5: supply line for steam, 2a, 3a, 4a: preheater, 5a: super-heated steam generator, 8: cooling means, 9: outlet line, 10: steam and acidic liquid-recovery tank, 11: alkaline cleaning device, 12: dehydrating tower, 20: reaction apparatus

What is claimed is:

1. A process for producing 2,3,3,3-tetrafluoropropene and 1,1-difluoroethylene from chlorodifluoromethane, chloromethane and tetrafluoroethylene, the process comprising:
   (a) supplying chlorodifluoromethane, chloromethane and tetrafluoroethylene to a reactor, as preliminarily mixed or separately,
   (b) supplying a heat medium to the reactor, and
   (c) contacting the heat medium with chlorodifluoromethane, chloromethane and tetrafluoroethylene in the reactor to form a reaction product comprising 2,3,3,3-tetrafluoropropene and 1,1-difluoroethylene.

2. The process according to claim 1, wherein a molar ratio of tetrafluoroethylene to chlorodifluoromethane supplied to the reactor ranges from 0.01 to 100.

3. The process according to claim 1, wherein a molar ratio of chloromethane to chlorodifluoromethane and tetrafluoroethylene in total supplied to the reactor ranges from 0.1 to 10.

4. The process according to claim 1, wherein chloromethane is supplied to the reactor at a temperature of from 0 to 1,200° C.

5. The process according to claim 1, wherein chlorodifluoromethane is supplied to the reactor at a temperature of from 0 to 600° C.

6. The process according to claim 1, wherein tetrafluoroethylene is supplied to the reactor at a temperature of from 0 to 1,200° C.

7. The process according to claim 1, wherein a temperature in the reactor in said contacting (c) is adjusted to be from 400 to 1,200° C.

8. The process according to claim 1, wherein the heat medium is supplied to the reactor at a temperature of from 100 to 1,200° C.

9. The process according to claim 1, wherein the heat medium is at least one selected from the group consisting of steam, nitrogen and carbon dioxide.

10. The process according to claim 1, wherein the heat medium is supplied at an amount of from 20 to 98 vol % in an entire gas supplied to the reactor.

11. The process according to claim 1, wherein gas supplied to the reactor has a contact time in the reactor of from 0.01 to 10 seconds.

12. The process according to claim 1, wherein a pressure in the reactor is from 0 to 2 MPa by gauge pressure.

13. The process according to claim 1, wherein at least one selected from the group consisting of chlorotrifluoroethylene, trifluoroethylene, hexafluoropropene and octafluorocyclobutane, is further supplied to the reactor.

14. The process according to claim 1, wherein
   the reaction product further comprises chlorotrifluoroethylene, and
   a molar ratio of 2,3,3,3-tetrafluoropropene to chlorotrifluoroethylene in the reaction product is ≥9.0.

15. The process according to claim 1, further comprising:
   (d) after said contacting (c), withdrawing from the reactor a reaction mixture comprising 2,3,3,3-tetrafluoropropene and 1,1-difluoroethylene formed in the reactor,
   wherein said supplying (a), said supplying (b), and said withdrawing (d) are continuously carried out.

* * * * *